(12) United States Patent
Sarstedt

(10) Patent No.: US 7,303,545 B2
(45) Date of Patent: Dec. 4, 2007

(54) PROTECTIVE HOUSING FOR A BUTTERFLY NEEDLE

(75) Inventor: Walter Sarstedt, Nümbrecht (DE)

(73) Assignee: Sarstedt AG & Co., Numbrecht (DE)

(*) Notice: Subject to any disclaimer, the term of this patent is extended or adjusted under 35 U.S.C. 154(b) by 45 days.

(21) Appl. No.: 10/496,176

(22) PCT Filed: Nov. 20, 2002

(86) PCT No.: PCT/DE02/04267

§ 371 (c)(1),
(2), (4) Date: Jun. 24, 2004

(87) PCT Pub. No.: WO03/045491

PCT Pub. Date: Jun. 5, 2003

(65) Prior Publication Data

US 2005/0038398 A1   Feb. 17, 2005

(30) Foreign Application Priority Data

Nov. 20, 2001  (DE) ............... 101 56 587

(51) Int. Cl.
*A61M 5/00* (2006.01)

(52) U.S. Cl. .............. 604/110; 604/263; 604/177; 604/198

(58) Field of Classification Search ........... 604/164.08, 604/177, 110, 198, 263
See application file for complete search history.

(56) References Cited

U.S. PATENT DOCUMENTS

| 5,433,703 A |   | 7/1995 | Utterberg et al. |
| 5,772,638 A | * | 6/1998 | Utterberg et al. ........... 604/263 |
| 5,779,679 A | * | 7/1998 | Shaw ........................ 604/158 |

FOREIGN PATENT DOCUMENTS

EP   0 436 646   8/1994

* cited by examiner

*Primary Examiner*—Catherine S. Williams
(74) *Attorney, Agent, or Firm*—Andrew Wilford

(57) ABSTRACT

A butterfly-needle set has an elongated two-part case forming a pair of transversely open slots. An elongated needle in the case has a pair of generally coplanar and oppositely projecting wings projecting out of the case through the slots. The slots are sufficiently long that the needle can move longitudinally between a front position with the needle projecting from a front end of the case and a rear position with the needle completely within the case. An elastically deflectable spring element projects at a small acute angle toward a rear end of the case into at least one of the slots so as to deflect elastically and allow the needle to move from the front position into the rear position and to block movement of the needle from the rear position into the front position.

9 Claims, 2 Drawing Sheets

US 7,303,545 B2

PROTECTIVE HOUSING FOR A BUTTERFLY NEEDLE

CROSS REFERENCE TO RELATED APPLICATIONS

This application is the U.S. national phase of PCT application PCT/DE2002/004267, filed 20 Nov. 2002, published 5 Jun. 2003 as WO 2003/045491, and claiming the priority of German patent application 10156587.9 itself filed 20 Nov. 2001.

FIELD OF THE INVENTION

The invention relates to a butterfly needle having a generally U-section and elongated lower shell and an elongated upper shell that are connected together to form the case after the butterfly needle is fitted to them and that form on each side a guide slot defining front and rear holding and retaining positions.

BACKGROUND OF THE INVENTION

In order to draw blood, a needle, which has an adapter that can be connected via tubing to the blood-drawing syringe, is used which has wings. In order to prevent the user from inadvertently getting stuck by the needle, such butterfly needles are provided with a shield case that encloses the needle.

Such a shield case is known from EP 0,436,646 (US equivalents U.S. Pat. No. 5,266,072 and U.S. Pat. No. 5,112,311). The needle in this system is pulled from the patient by the tube connected to the needle. In order to protect the user from needle sticks, the pulled-back needle is held in a protected position. In order to secure the protection, an anchor part is pressed against the patient. Such a procedure reduces or minimizes the risk of an undesired needle stick for the user.

In this known embodiment the butterfly needle is pulled directly out of the skin of the patient into the protected position inside the shield case.

Such a procedure is difficult for the patient since the anchor part has to be pressed with one hand against the skin of the patient while simultaneously the tube is pulled with the other hand. There is the possibility that the needle, which to this time is still in the blood vessel of the patient, moves. This movement can be painful.

OBJECT OF THE INVENTION

It is an object of this invention to simplify the operation of a protective case of this type such that when pulling out the butterfly needle there is no resistance to overcome and the withdrawal of the needle can take place in the position the needle has assumed in the vein.

SUMMARY OF THE INVENTION

This object is achieved in that vertical side walls of the shells form guide grooves through which the wings project on both sides of the case and a spring element projecting from at least one of the side walls into the respective groove defines a retaining seat for the butterfly needle.

In one embodiment the upper shell is narrower than the lower shell so that the guide slots form vertically and horizontally open gaps on both sides between the adjacent vertical side walls of the shells. A spring element projects from at least one side wall of one of the shells into the respective guide slot and arrests the butterfly needle in the rear retaining position.

The front holding position for the butterfly needle is defined by a holding formation projecting from inside the upper or lower shell or from both shells and that engages a middle region of the butterfly needle. This holding formation can be formed for example as one or more bumps or ridges.

BRIEF DESCRIPTION OF THE DRAWING

Further embodiments and advantages of the invention are seen in the claims and the following description of an embodiment of the invention shown in the drawing. Therein:

SPECIFIC DESCRIPTION

Figure 1:
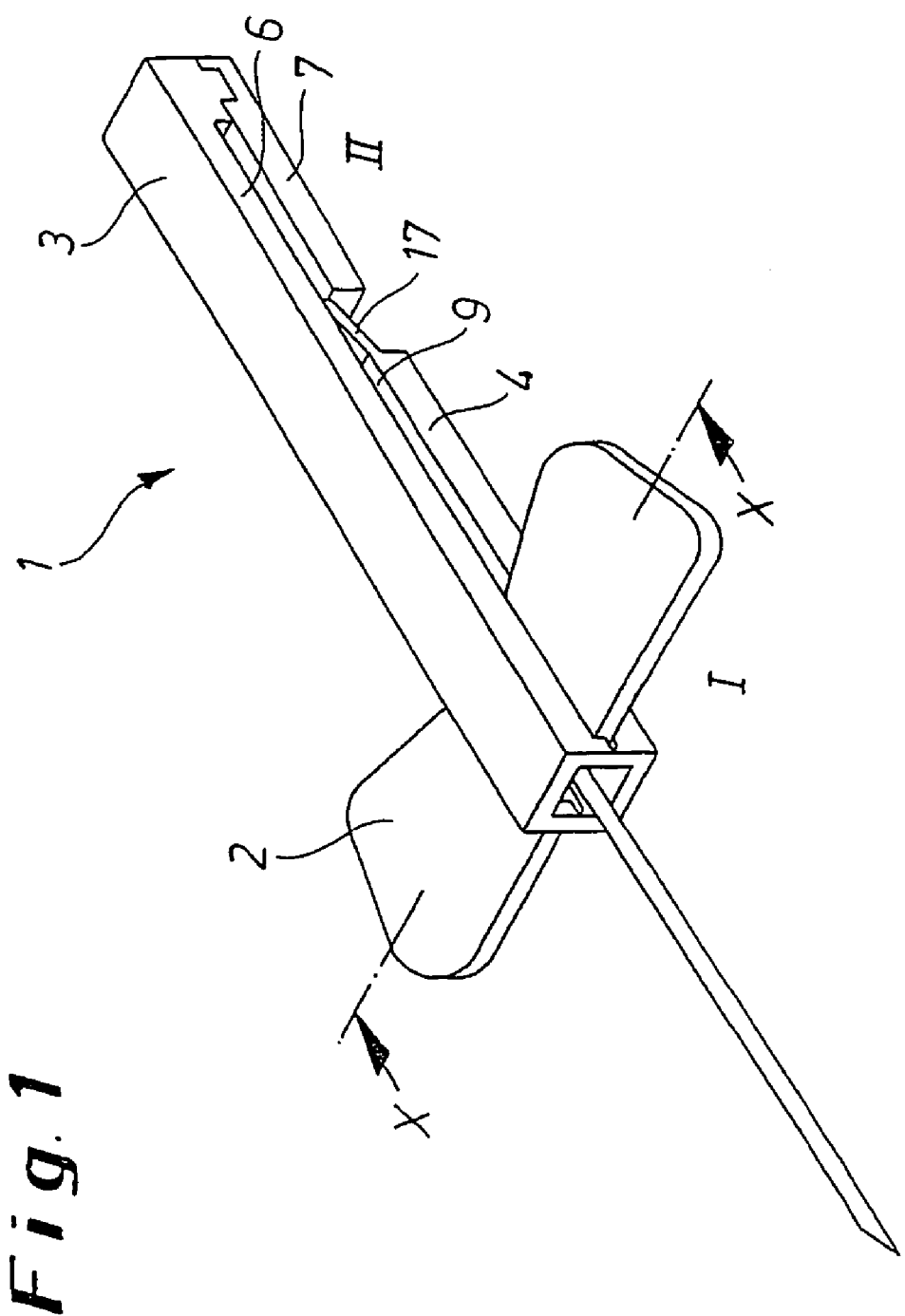
FIG. 1 is a perspective side view of a blood-drawing set comprised of a butterfly needle and its shield case.
Figure 2:
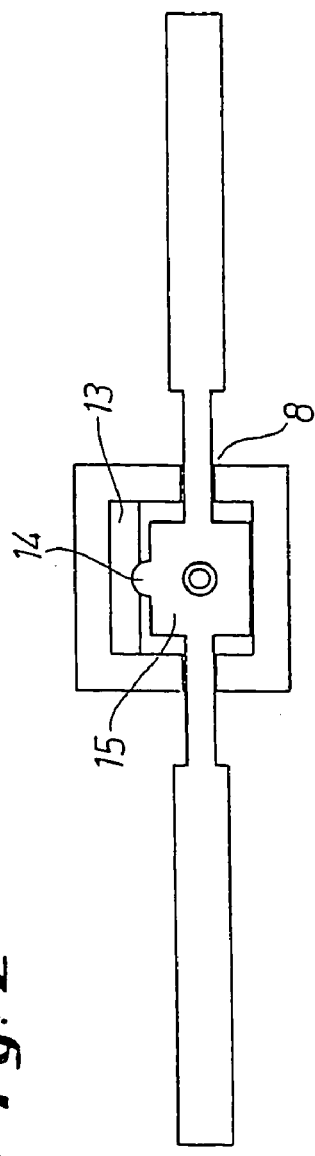
FIG. 2 is a section taken along line X-X of FIG. 1.
Figure 3:
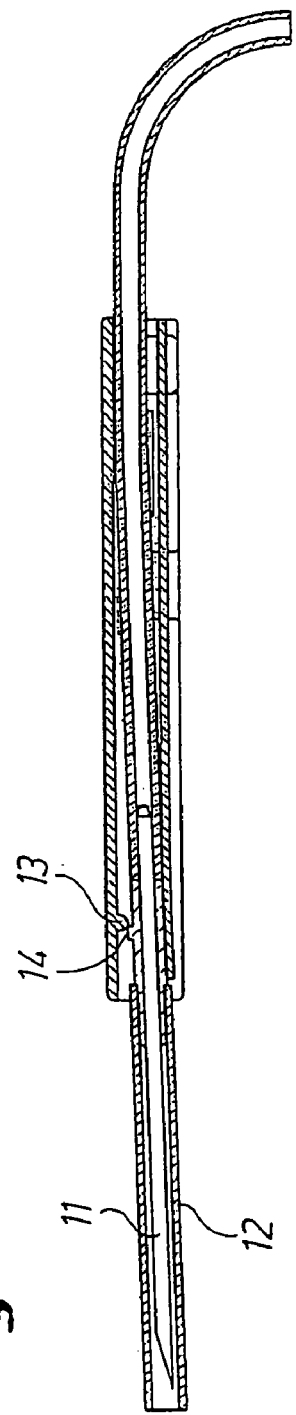
FIG. 3 is a longitudinal section through the blood-drawing set of FIG. 1.

FIG. 1 shows a conventional blood-drawing set comprised of a butterfly needle 2 held inside a shield case 1. The shield case 1 is comprised of an upper shell 3 and a lower shell 4. In the illustrated embodiment the upper shell 3 and the lower shell 4 are of the same width. It is however also possible to make the upper shell 3 narrower than the lower shell 4.

The upper shell 3 can be connected with the lower shell 4 by, for example, a membrane hinge. After fitting the butterfly needle 2, the upper shell is locked to the lower shell 4 by, for example, a barb connection.

It is also possible to lock the upper and lower shells 3 and 4 together at both edges. Spaced side walls 6 and 7 of the upper and lower shells 3 and 4 form horizontal gaps 8 that in turn constitute guide slots 9 for the wings of the needle 2.

If the upper shell 3 is narrower than the lower shell 4, there will be the horizontally open gaps 8 as well as vertically open gaps through which the wings of the needle 2 extend.

In the starting position of the butterfly needle 2, that is the position in which the set is supplied to the user, the needle 11 is covered by a guard tube 12. An elastic web or bump 13 holds the butterfly needle 2 by engagement with a raised part 14 in a central region 15 of the butterfly needle 2.

After drawing blood, the butterfly needle 2 is pulled out of the patient's vein. As it is pulled back the bump 14 of the middle part 15 of the butterfly needle 2 moves under the elastically deformable bump 13. The wings fit at the end of the guide groove 9 into a retaining seat II defined by spring elements 17 projecting into the guide groove. The spring elements 17 are easily pushed down by the passing wings.

The invention claimed is:

1. A butterfly-needle assembly comprising:
    an elongated and generally U-section lower case part having a pair of longitudinally extending vertical side walls;
    an elongated upper case part extending longitudinally along the lower part and forming a pair of transversely open slots with the side walls thereof, the case parts together forming an elongated hollow case;
    an elongated needle in the case and having a pair of generally coplanar and oppositely projecting wings extending out of the case through the slots, the slots being sufficiently long that the needle can move longitudinally between a front position with the needle projecting substantially from a front end of the case and a rear position with the needle completely within the case;

an elastically deflectable spring element projecting at a small acute angle toward a rear end of the case into one of the slots, extending at least partially across and blocking the one slot rearward of the respective wing in the front position of the needle, and directed to be deflected elastically by the respective wing and allow the needle to move from the front position into the rear position and to block movement of the needle from the rear position into the front position;

a case formation projecting transversely inwardly into the case; and a needle formation projecting transversely outwardly from the needle opposite to the case formation and being longitudinally engageable with the case formation on shifting of the needle between its position, the case and needle being sufficiently elastically deformable that the formations can push longitudinally past each other on longitudinal shifting of the needle between its positions, the formations being positioned to retain the needle in the front position and prevent displacement of the needle forward out of the case.

2. The butterfly-needle assembly defined in claim 1 wherein the spring element is formed unitarily with the case.

3. The butterfly-needle assembly defined in claim 1 wherein the slots are of substantially uniform height.

4. The butterfly-needle assembly defined in claim 1, wherein each slot has one such spring element engageable with the respective wing.

5. The butterfly-needle assembly defined in claim 1 wherein the spring element is a finger formed unitarily with one of the side walls.

6. The butterfly-needle assembly defined in claim 1, further comprising tubing connected to a rear end of the needle and extending out of a rear end of the case.

7. The butterfly-needle assembly defined in claim 1 wherein the formations include an inwardly projecting bump on the case and an outwardly projecting bump on the needle.

8. The butterfly-needle assembly defined in claim 1 wherein the slots are straight and of uniform transverse height.

9. The butterfly-needle assembly defined in claim 7 wherein the slots extend parallel to a longitudinal displacement direction of the needle in the case.

* * * * *